(12) United States Patent
Findeisen et al.

(10) Patent No.: US 9,068,824 B2
(45) Date of Patent: Jun. 30, 2015

(54) STEREOSCOPIC ENDOSCOPE FOR MEASURING A THREE DIMENSIONAL SURFACE

(75) Inventors: Charles Findeisen, Wettingen (CH); Bruno Knobel, Laufen (CH); Christof Ballweg, Laufen (CH)

(73) Assignee: Naviswiss AG, Laufen (CH)

( * ) Notice: Subject to any disclaimer, the term of this patent is extended or adjusted under 35 U.S.C. 154(b) by 154 days.

(21) Appl. No.: 13/391,128

(22) PCT Filed: Aug. 20, 2010

(86) PCT No.: PCT/EP2010/005128
§ 371 (c)(1),
(2), (4) Date: Mar. 7, 2012

(87) PCT Pub. No.: WO2011/023339
PCT Pub. Date: Mar. 3, 2011

(65) Prior Publication Data
US 2013/0030250 A1    Jan. 31, 2013

(30) Foreign Application Priority Data
Aug. 27, 2009  (DE) .......................... 10 2009 038 755

(51) Int. Cl.
*A61B 1/06*    (2006.01)
*G01B 11/25*   (2006.01)
(Continued)

(52) U.S. Cl.
CPC .......... *G01B 11/2513* (2013.01); *A61B 5/1079* (2013.01); *A61B 1/00096* (2013.01); *A61B 1/00183* (2013.01); *A61B 1/00193* (2013.01); *A61B 1/07* (2013.01); *A61B 1/3132* (2013.01);

*A61B 5/1077* (2013.01); *G02B 23/2415* (2013.01); *G02B 23/2476* (2013.01); *A61B 1/00165* (2013.01)

(58) Field of Classification Search
CPC ........... A61B 1/00071; A61B 1/00096; A61B 1/00193; A61B 1/00183; A61B 1/3132; A61B 5/1077; A61B 5/1079; G02B 23/2415; G01B 11/2513
USPC .................................. 600/111, 129, 166, 174
See application file for complete search history.

(56) References Cited

U.S. PATENT DOCUMENTS 5,090,400 A * 2/1992 Saito .............................. 600/108
5,166,787 A * 11/1992 Irion ............................... 348/75
(Continued)

FOREIGN PATENT DOCUMENTS

| DE | 4130237 A1 | 3/1993 |
| JP | 1242033 A | 9/1989 |
| WO | 97/14932 A1 | 4/1997 |

OTHER PUBLICATIONS

International Search Report dated Dec. 22, 2010 from PCT/EP2010/005128.

*Primary Examiner* — John P Leubecker
(74) *Attorney, Agent, or Firm* — Ohlandt, Greeley, Ruggiero & Perle, L.L.P.

(57) ABSTRACT

An endoscope having two entry lenses, which are arranged spaced from each other and the fields of view of which overlap, and having guiding devices. The entry lenses are spaced so far apart from each other that the outer edges thereof protrude beyond the cross-sectional area of the guiding devices, and a lens displacing the axis beam is inserted between one entry lens and the guiding devices. A method for the use of the endoscope.

9 Claims, 7 Drawing Sheets

(51) Int. Cl.
    *A61B 5/107* (2006.01)
    *A61B 1/00* (2006.01)
    *A61B 1/313* (2006.01)
    *G02B 23/24* (2006.01)
    *A61B 1/07* (2006.01)

(56) References Cited

U.S. PATENT DOCUMENTS

| | | | |
|---|---|---|---|
| 5,305,121 A * | 4/1994 | Moll | 348/45 |
| 5,368,015 A * | 11/1994 | Wilk | 600/104 |
| 5,928,137 A | 7/1999 | Green | |
| 6,066,090 A * | 5/2000 | Yoon | 600/113 |
| 6,277,064 B1 * | 8/2001 | Yoon | 600/114 |
| 6,976,956 B2 | 12/2005 | Takahashi et al. | |
| 8,556,806 B2 * | 10/2013 | Farr | 600/160 |
| 8,562,513 B2 * | 10/2013 | Yamatani | 600/106 |
| 2005/0234296 A1 | 10/2005 | Saadat et al. | |
| 2007/0049794 A1 * | 3/2007 | Glassenberg et al. | 600/109 |
| 2007/0173688 A1 * | 7/2007 | Kim | 600/111 |
| 2007/0287889 A1 * | 12/2007 | Mohr | 600/207 |
| 2008/0027279 A1 * | 1/2008 | Abou El Kheir | 600/111 |
| 2008/0071289 A1 * | 3/2008 | Cooper et al. | 606/130 |

* cited by examiner

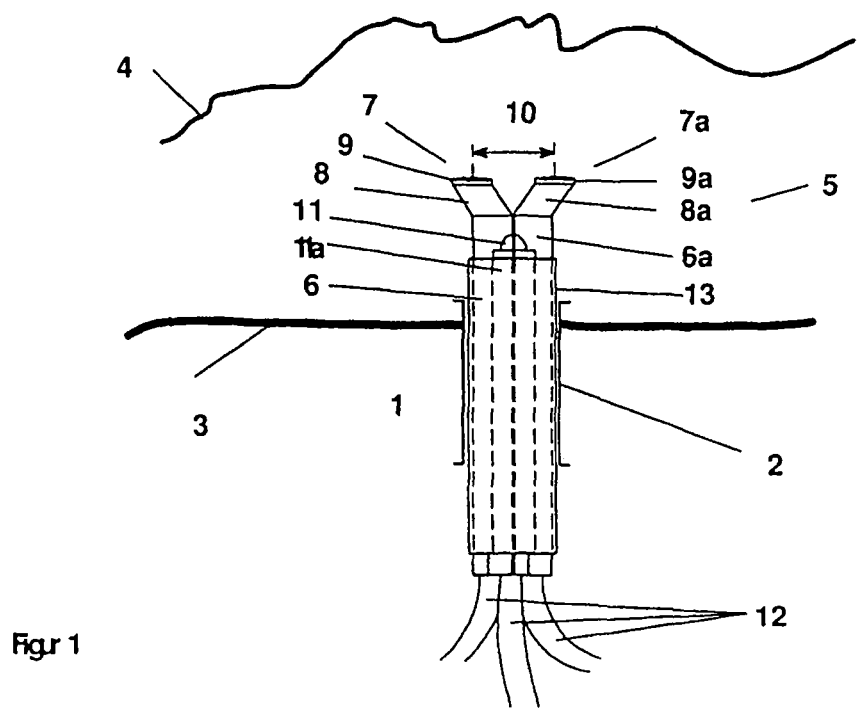
Fig. 1
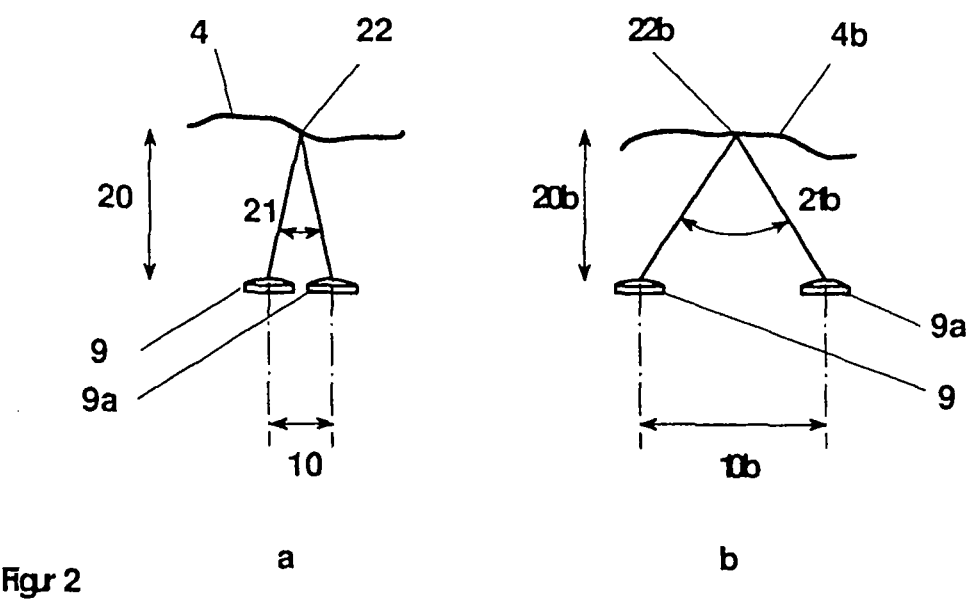
Fig. 2          a                    b

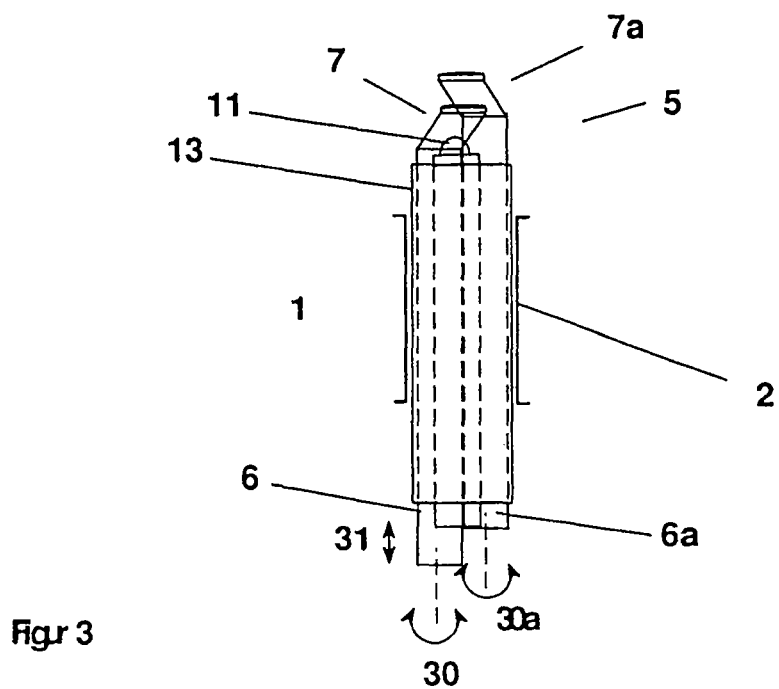
Fig.r 3

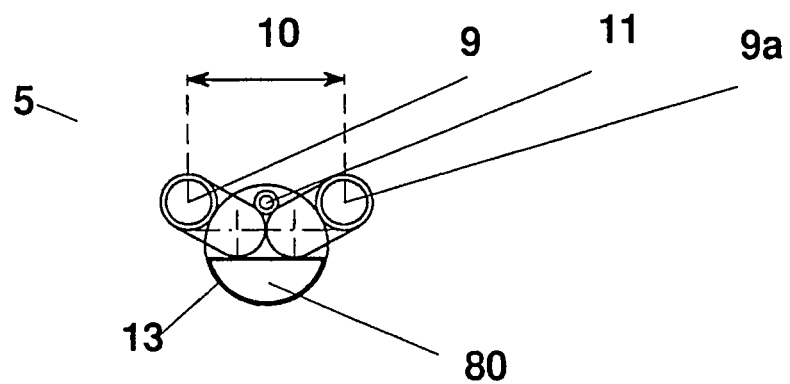
Fig.r 8
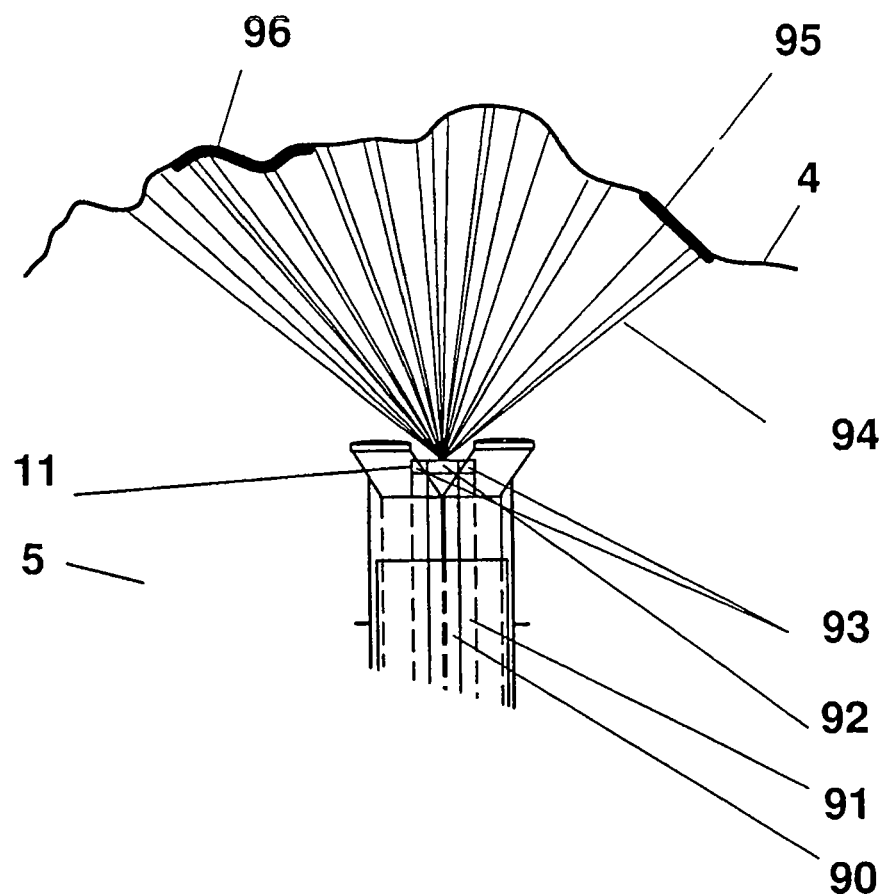
Fig.r 9

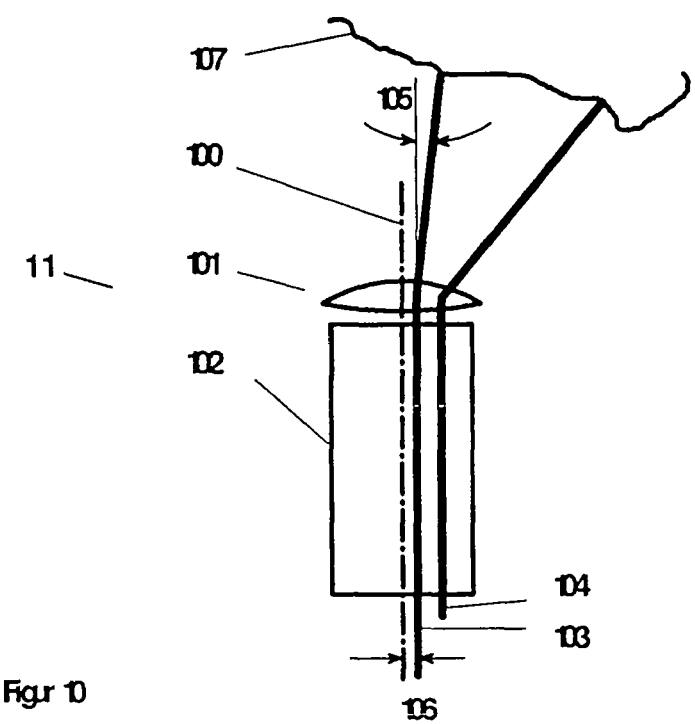
Figur 10

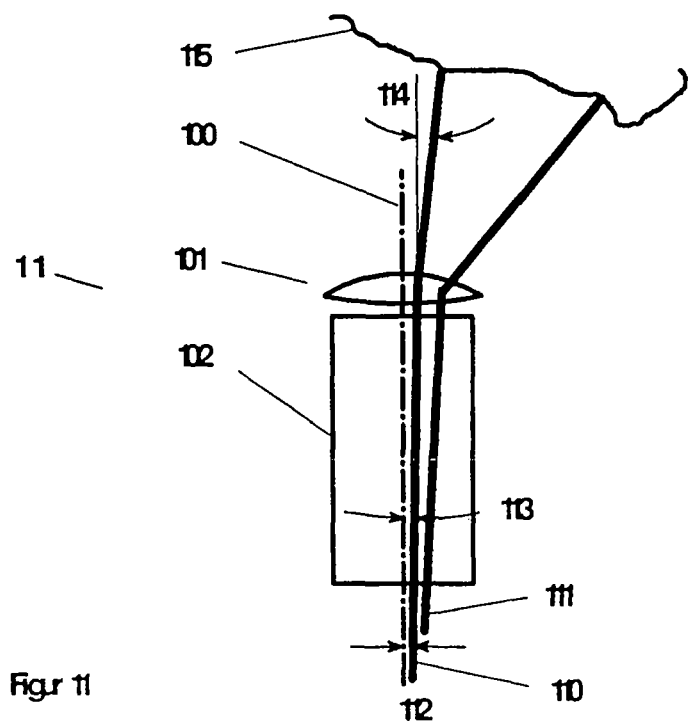
Figur 11
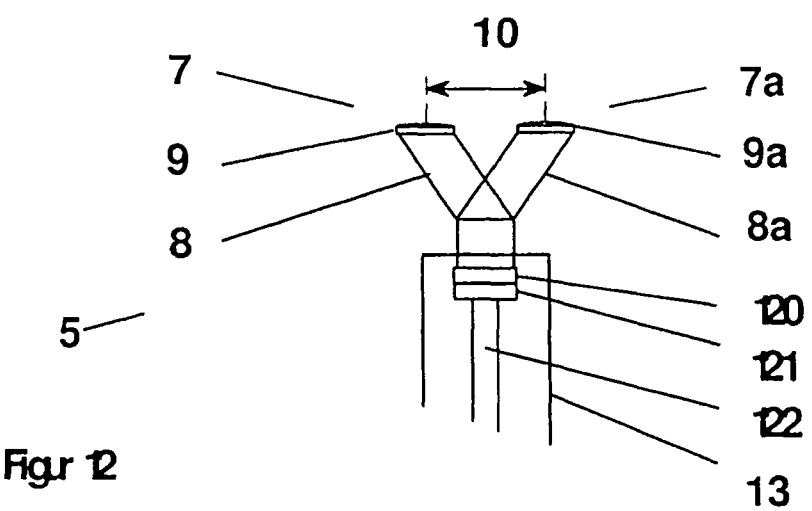
Figur 12

STEREOSCOPIC ENDOSCOPE FOR MEASURING A THREE DIMENSIONAL SURFACE

BACKGROUND

1. Field

The invention relates to an endoscope with two entry lenses which are arranged spaced from each other and the fields of view of which overlap and with guiding devices. The invention more specifically relates to stereometric endoscopes with a modifiable base for medical uses, more specifically in surgery with illumination of the upper side of the object and with optional projection of structured light onto the upper side of the object.

2. Discussion of the Background Art

Endoscopes are indispensable for minimally invasive operation techniques. With endoscopy, optical systems can be introduced through the smallest main orifices into the body of humans or animals.

Special techniques allow combining optical systems (image guides and illumination) with mechanical instruments. In laparoscopy for instance, a tube is inserted into the abdomen of the patient. A gas ($CO_2$) is often pumped into the abdomen through the tube, which is sealed off relative to the abdominal wall, so that the abdominal wall lifts off the organs. A hollow cavity is thus formed, in which it becomes possible to orient oneself by means of adapted optical systems. Mechanical instruments as well as illumination and imaging systems are introduced into the tube. The surgeon can conduct minimally invasive surgical interventions on the patient.

An endoscope is an image guide with an entry lens at the distal end of the image guide and an exit lens at the other end of the image guide. An entry lens with a great aperture angle is often needed in order to be able to orient oneself. Depth information can only be deduced in a limited manner, for instance via known structures or by using the endoscope with the aid of an externally attached navigation system.

Stereometrically operating endoscopes are based on two optical axes residing in the endoscope tube. By using these two lens systems, it is basically possible to operate stereometrically. Both optical axes are located directly next to each other. The angle of vision between the optical axis of the first image guide relative to the object and the optical axis of the second image guide is small. This is why only very inaccurate depth information can be obtained.

The published patent application DE 39 212 33 A1 describes an endoscope with a video device disposed at the distal end. This endoscope is characterized in that at least the objective and image receiver are combined into a video unit, which after insertion into the cavity to be observed, is movable as a whole relative to the distal end of the endoscope shaft. Two such video units allow a stereo observation with a widened base.

The published patent application WO 2010/020397 A1 presents a stereo endoscope in combination with patterns attached to objects. The photogrammetric analysis of the stereo images describes the surface topology of the measured object in three dimensions by means of the patterns previously attached to the surface. Freeform surfaces that are not completely equipped with patterns can only be measured in a limited manner with this assembly.

The invention is based on the idea that with stereoscopically disposed endoscopes a substantial improvement of the depth information is achieved by means of an increased distance between the entry objectives. Furthermore, natural structures and/or flexible and/or rigid patterns previously disposed on surfaces of objects are measured in three dimensions by means of an optional illumination of the measuring volume. In addition, by means of an optional projection of structured light onto the surface of an object, its three-dimensional topology is recorded and is related to the patterns and/or the natural structures.

The object of the invention is to further develop an endoscope in order to measure more specifically the surface topology of objects in cavities.

SUMMARY

In a preferred design an illumination device, which emits structured light is integrated into the endoscope.

A lens, which parallelly displaces the axial beam, is preferably fitted between the entry lens and the guiding devices. A lens, which parallelly displaces the axial beam, is for instance a rhomboid prism or a mirror pair.

At least a part of the lens is preferably provided with a coating, which reduces the surface tension.

A particularly preferred embodiment provides that the entry lenses can be disposed at a defined variable distance from each other by means of a device integrated into the guiding devices.

Another embodiment of the invention provides that, if required, the entry lenses and the lenses, which parallelly displace the axial beam, take up a surface, the outer edge of which does not protrude over the cross-sectional surface of the guiding devices.

A particularly advantageous embodiment provides that the optical axes of the entry lenses are spaced apart by at least two and a half times the diameter of the cross-section at the narrowest point of the guiding devices.

The structured light is preferably generated by means of laser light and a diffractive optical element (DOE).

The structured light is preferably generated by means of light beams, which are guided in a defined manner in the image guide equipped with an entry lens and an exit lens. These light beams are white or colored as required.

Another embodiment of the invention provides that the lenses displacing the axial beam are disposed on a common imaging sensor.

The present invention presents a method for use of an endoscope described in claim 1 and in further sub-claims, with the features of patent claim 11. Images of surfaces of objects which are lighted and/or illuminated by means of structured light are thereby photogrammetrically analyzed and these surfaces of objects are made available as a three-dimensional point cloud.

The method provides that the endoscope gives an optical reference in order to implement a precise measuring of the surface topology of at least one object relative to a coordinate system, which is defined by natural structures on the object or by flexible and/or rigid patterns applied onto the object's surface.

The method provides that the entry lenses and the lenses parallelly displacing the axial beam, the outer edges of which do not protrude over the surface of the cross-section of the guiding devices, are positioned in a measuring position through a lead-in tube, that the entry lenses are then spaced apart in a defined manner at such a distance that their outer edges protrude over the surface of the cross-section of the guiding devices, that a pattern and/or a natural structure is lighted and/or a structured light is projected onto the surface of the object, that the light reflected by the surface of the object is analyzed photogrammetrically and is made available as a three-dimensional point cloud in relation to the patterns and/or natural structures. The surface of the object can be illuminated with white light.

Another embodiment of the invention provides that at least one pattern is disposed on the surface of the object.

While measuring the topology of the surface of the object, the endoscope is preferably guided manually.

The invention is not only adapted for medical use. The system can be used whenever the endoscope must be introduced through a narrow hole and whenever there is more space in the actual measuring area, in order to obtain precise measuring results of surfaces and forms.

BRIEF DESCRIPTION OF THE DRAWINGS

In the following the invention is described without limitation of the general idea of the invention by means of exemplary embodiments with reference to the figures, which also disclose all the particulars of the invention that are not explained in detail in the text. In the drawings:

FIG. 1 schematically shows a lateral view of the endoscope in situ in the opened state, FIG. 2 schematically shows two differently sized spacings between pairs of entry lenses, FIG. 3 schematically shows the lateral view of the endoscope in the closed state, FIG. 4 schematically shows the lateral view of the individual components in the closed state, FIG. 5 schematically shows the lateral view of the components for the illumination device, FIG. 6 schematically shows the top view of the optical system in the closed state, FIG. 7 schematically shows the top view of the optical system in the opened state, FIG. 8 schematically shows the top view of the optical system in the opened state with a freed passage for additional instruments, FIG. 9 schematically shows the lateral view of an illumination device for illuminating an object with natural structures and applied patterns and for structured light generated by means of a diffractive optical element and a laser beam, FIG. 10 schematically shows the lateral view of another embodiment of an illumination device with two light beams, which are parallel to the image guide axis, FIG. 11 schematically shows the lateral view of another embodiment of an illumination device with two light beams, which do not run parallel to the image guide axis, FIG. 12 schematically shows the lateral view of another embodiment of an endoscope in the opened state with an imaging sensor integrated in the optical head.

DETAILED DESCRIPTION OF THE PREFERRED EMBODIMENT

Figure 4:
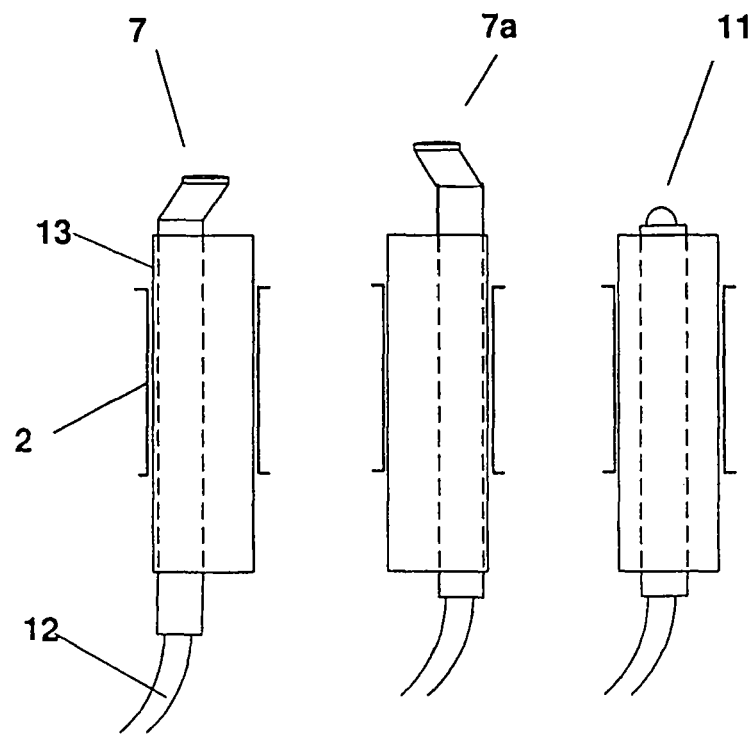

In the following, the endoscope is exemplified for laparoscopic use. Laparoscopy refers to a method in which the abdominal cavity and the organs located therein are made visible with special rod lens optical systems (for rigid endoscopes) through small orifices made by the surgeon in the abdominal wall. Using endoscopes with flexible image guides instead of endoscopes with rigid rod lens optical systems is also possible.

FIG. 1 schematically shows the lateral view of the endoscope 1 in situ in the opened state. The optical system 5 is positioned in front of the object 4 to be examined. The image and light guides 6, 6a, 11a of the guiding devices between the optical system 5 and the external supply module 12 are integrated in the tube 13. The tube 13 is located inside the lead-in tube 2 leading through the abdominal wall 3.

Each of the two optical heads 7 or 7a consists of a lens 8 or 8a parallelly displacing the axial beam and an entry lens 9 or 9a. The lens 8 or 8a parallelly displacing the axial beam is for instance a pair of mirrors or a rhomboid prism. For measuring, the spacing 10 between the optical axes of the entry lenses 9 and 9a is adjustable in a defined manner by means of mechanical devices integrated in the guiding devices. Positioning the optical heads 7 and 7a can occur for instance by rotating and/or displacing the image guides 6 and 6a. In the opened state, the endoscope 1 cannot be removed from the lead-in tube 2. The opened state means that the optical heads 7 and 7a are in positions where they are ready for measuring.

The illumination device 11 illuminates the object's surface 4. The illumination device can optionally be positioned at about the same level as the entry lenses 9 and 9a. The illumination device 11 serves to illuminate the object's surface 4 and/or to scan and record the surface 4 by means of structured light. The illumination device 11 is connected to the external supply modules 12 by means of light and/or image guides 11a integrated in the guiding devices.

The external supply module 12 serves to supply the illumination device 11 with the necessary light and to receive the video signals from the entry lenses 9 and 9a. The images can be directly viewed visually. The video signals can be recorded with imaging sensors and analyzed photogrammetrically. The external supply module 12 furthermore contains devices for mechanically moving the optical heads 7 and 7a.

The FIGS. 2a and 2b schematically show the impact of the spacing 10 or 10b of the pair of entry lenses 9 and 9a on the precision of the depth information. FIG. 2a schematically shows a metrologically unfavorable situation with an acute angle 21, which is defined by the spacing 10 and the distance 20. The distance 20 is the average spacing of the pair of entry lenses relative to the point 22 on the surface 4 of the object. FIG. 2b schematically shows a metrologically favorable situation with a wide angle 21b, which is defined by the great spacing 10b and the relatively smaller distance 20b to the point 22b on the surface 4b.

FIG. 3 schematically shows the lateral view of the endoscope 1 in the closed state. The optical heads 7 and 7a are thereby rotated by angles 30 and 30a. One of the two image guides 6 or 6a can optionally be displaced along its axis by the distance 31. In the closed state, the endoscope 1 can be easily taken out of the stationary lead-in tube 2 or pushed into the measuring site. In the state of insertion through the lead-in tube 2, the optical heads 7 and 7a are positioned in such a way that their outer edges do not protrude over the cross-sectional surface of the guiding devices, which is given by the tube 13. In the operating state, i.e. in the opened state, both optical heads are turned outward by angles 30 and 30a and optionally longitudinally displaced by the distance 31. The rotational movement of both image guides 6 and 6a by the angles 30 and 30a typically lies in the range of 140 to 170 degrees, in order to obtain an optimal spacing for measuring between the pair of entry lenses. After the rotational movement by the angles 30 and 30a and the longitudinal displacement by the distance 31, the entry lenses 9 and 9a are symmetric relative to the illumination device 11.

During use, the optical system 5 is pushed into the lead-in tube 2 with turned-in optical heads 7 and 7a. Inside the abdominal cavity, the optical heads 7 and 7a are now turned outward laterally by the angles 30 or 30a and optionally longitudinally displaced by the distance 31, so that their entry lenses 9 and 9a form a spacing of the pair of entry lenses that is optimal for measuring.

The rotational movements of the image guides and the optional longitudinal movement of one of the two image guides can occur with precision and free of clearance via the mechanical guides specifically provided for this. The endoscope can thereby be calibrated for optical measuring in the opened state. After shifting into the closed state and reopening, the system calibration is still valid. The closed state means that the optical heads 7 and 7a are not in the positions in which they are ready to measure. In the closed state, the outer edges of the optical heads 7 and 7a do not protrude over the cross-sectional surface of the guiding devices.

FIG. 4 schematically shows the individual components of the endoscope described in the FIGS. 1 and 3 in a lateral view.

Figure 5:
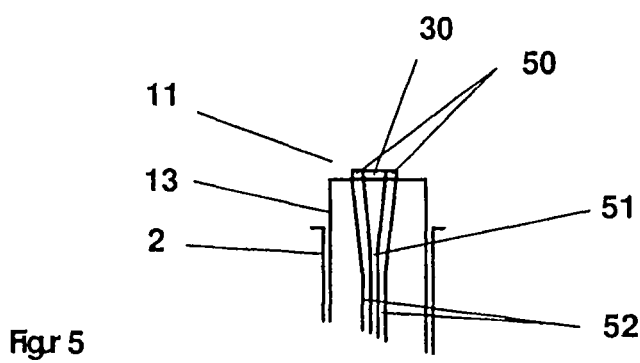

FIG. 5 schematically shows the lateral view of further details of the illumination device 11 of the endoscope. The exit lens 50 and the light guide 52 serve for illuminating the surfaces of objects with preferably white light. The diffractive optical element 30 with the light guide 51 for supplying the laser beam serve for projecting structured light onto the surface of the object. The tube 13 containing all the guiding devices that is located in the lead-in tube 2 is shown schematically.

Figure 6:
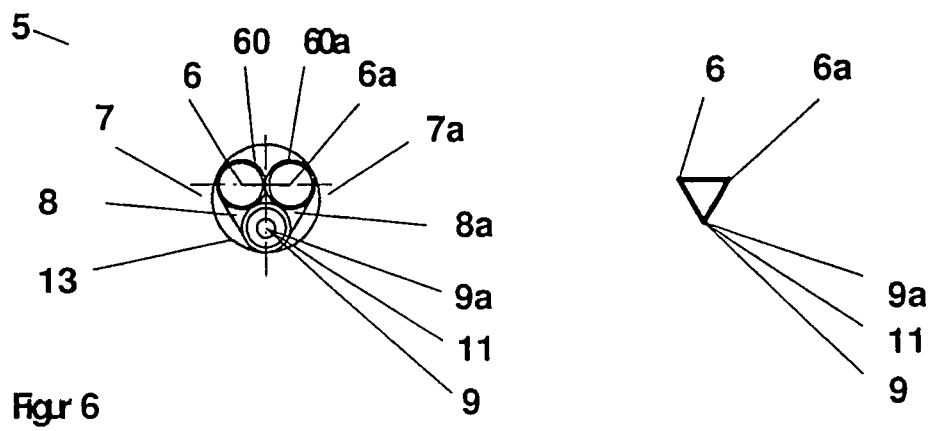

FIG. 6 on the left schematically shows the top view of the optical system 5 in the closed state. The optical axes of the entry lenses 9 and 9a as well as of the illumination device 11 are located close to each other in the top view. The optical head 7 or 7a with the lens 8 or 8a, which parallelly displaces the axial beam, is configured in such way that in the closed state, the outer edges do not protrude over the cross-sectional surface of the guiding devices in the tube 13. The optical head 7 or 7a can be opened and closed by means of the sleeve 60 or 60a enveloping the image guide 6 or 6a. In the closed state, the illumination device 11 is covered by the optical heads 7 and 7a.

FIG. 6 on the right schematically shows a top view of the central axes of both image guides 6 and 6a and the optical axes of the illumination device 11 and of both entry lenses 9 and 9a in the closed state.

Figure 7:
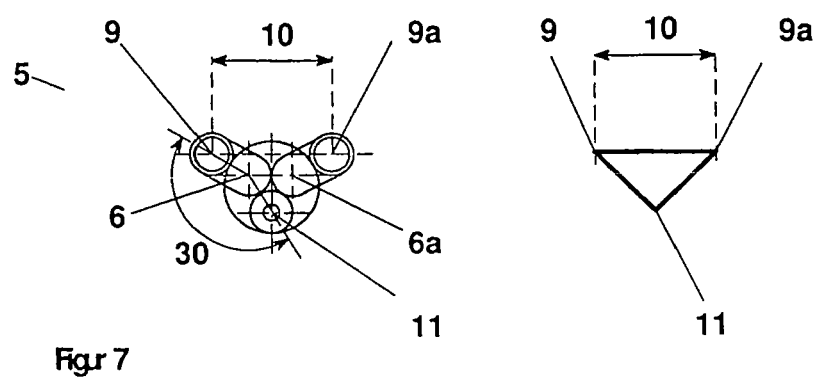

FIG. 7 on the left schematically shows the top view of the optical system 5 in the opened state. The rotational angle 30 around the axis of the image guide 6 is exemplarily marked. At the spacing 10, the optical axes of the entry lenses 9 and 9a are at a maximal distance from each other.

FIG. 7 on the right schematically shows the optical axes of both entry lenses 9 and 9a spaced apart by the spacing 10 in a top view of the optical system in an opened state. In the opened state, the illumination device 11 is not covered by the optical heads.

FIG. 8 schematically shows the top view of the optical system 5 in the opened state with another embodiment of the illumination device 11. Further instruments for instance can be inserted into the cavity with the object through the passage 80 in the tube 13. At the spacing 10, the optical axes of the entry lenses 9 and 9a are at a maximal distance from each other.

FIG. 9 schematically shows the lateral view of the optical system 5 with an illumination device 11 with a diffractive optical element 92 that divides the laser beam that has been guided through the light guide 90 into structured light 94. The structured light 94 projects patterns of dots and/or dashes onto the surface 4. The measuring volume with natural structures 96 present on surfaces of objects and/or flexible and/or rigid patterns attached to surfaces of objects is illuminated by the optical elements 93 and the image guide 91. It is advantageous to use colored structured light and white light for the illumination.

FIG. 10 schematically shows the lateral view of another embodiment of an illumination device 11 for structure light. Both exemplarily drawn light beams 103 and 104 run parallel to the optical axis 100 of the image guide 102. The lens 101 deflects the parallel light beams. The light beam 103 with a distance 10 from the optical axis 100 of the image guide 102 is for instance deflected by the lens 101 by the angle 105. The angle of deflection 105 preferably depends on the distance 106. By changing the distance 106 and thereby causing a continuous movement of the light beam, light patterns, which continuously move in the cavity, can be generated with the lens 101. Systematically moving light beams are thereby projected onto the surface of the object to be measured without moving the endoscope. Generating parallel light beams at a distance 106 relative to the optical axis 100 is prior art and is not further described here.

FIG. 11 schematically shows the lateral view of another illumination device 11 for structure light. The two exemplarily marked light beams 110 and 111 do not run parallel to the optical axis 11 of the image guide 102. The lens 101 deflects the light beams. The light beam 110 with a distance 112 and an angle 113 relative to the optical axis 102 is for instance deflected by the angle 114. In this exemplary embodiment, the angle of deflection 114 depends on the distance 112 and the angle 113. By continuously changing the distance and/or the angle, systematically moving light beams are projected onto the object surface 115 to be measured without moving the endoscope. Generating light beams that are not parallel to the optical axis 100 of the image guide 102 at a distance 112 and an angle 113 is prior art and is not further described here.

FIG. 12 schematically shows the lateral view of another embodiment of an optical system 5 with the optical heads 7 and 7a of an endoscope in the opened state. The imaging sensor 120 and corresponding electronic module 121 is integrated in the optical system 5. The visible surface of the object is displayed on the common imaging sensor 120 via the entry lenses 9 and 9a and the lenses 8 and 8a, which parallelly displace the axial beam. The distance 10 between the optical axes of the entry lenses 9 and 9a is adjustable in a defined manner for measuring. The guiding device 122 in the tube 13 of the endoscope connects the electronic module 121 with the supply module not shown in the figure. The illumination device is not shown.

The invention claimed is:

1. A medical stereoscopic endoscope for measuring a three dimensional surface of an object, comprising:
   a tube;
   two entry lenses, which are arranged spaced from each other and the fields of view of which overlap;
   guiding devices disposed in the tube for rotation and translation of the entry lenses relative to the tube, between a first position wherein the entry lenses are spaced apart by a distance so that that outer edges of the entry lenses protrude over the cross-sectional surface of the tube and a second position wherein the entry lenses are spaced apart by a distance so that outer edges of the entry lenses do not protrude over the cross-sectional surface of the tube;
   an optical displacement element that displaces the axial beam being inserted between an entry lens and the guiding devices, wherein for optical measurements, the entry lenses can be disposed at a defined variable distance from each other by means of mechanical devices integrated into the guiding devices, the entry lenses being positioned by rotating, so that the spacing between the optical axes of the entry lenses is adjustable in a defined manner by means of the devices; and an illumination device disposed in the tube for illuminating the fields of view of the entry lenses with structured light and with illuminating light to illuminate an observed structure with a pattern of the structured light and with the illuminating light, wherein the guiding devices are rotatable so that the entry lenses are positioned over the illumination device.

2. The endoscope according to claim 1, wherein at least a part of the entry lenses is equipped with a coating, which reduces the surface tension.

3. The endoscope according to claim 1, wherein optical axes of the entry lenses are spaced apart by at least two and a half times the diameter of the cross-section at the narrowest point of the guiding devices.

4. The endoscope according to claim 1, wherein the structured light is generated by means of laser light and a diffractive optical element.

5. The endoscope according to claim 1, wherein the structured light is generated by means of light beams, which are guided in a defined manner in an image guide equipped with an entry lens and an exit lens.

6. The endoscope according to claim 1, wherein at least one of mechanical devices is for rotation and displacement of the entry lenses to facilitate calibration of an optical measurement in the first position, rotation of the entry lenses to the second position, and maintaining the calibration when the entry lenses are rotated to the first position.

7. The endoscope according to claim 1, further comprising imaging sensors for receiving images of the three dimensional surface.

8. The endoscope according to claim 1, further comprising a supply module including imaging sensors for receiving images of the three dimensional surface for purposes of photogrammetrically analyzing the images.

9. An endoscope comprising:
a tube;
two light guides disposed in the tube, each light guide having an entry lenses, the light guides being configured so that the entry lenses are spaced from each other and have fields of view which overlap;
an optical displacement element inserted between an entry lens and the light guides for displacing light travelling along a light guide so that the light continues to travel parallel in an initial direction of travel and along the light guide;
the light guides being positioned in the tube so that the tube receives the light guides so that the light guides can be rotated and displaced along their lengths, relative to the tube, the entry lenses being spaced apart by a distance so that outer edges of the entry lenses protrude over the cross-sectional surface of the endoscope and the optical displacement element, wherein for optical measurement, the entry lenses can be disposed at a defined variable distance from each other so that the spacing between the optical axes of the entry lenses is adjustable; and
an illumination device disposed in the tube for illuminating the fields of view of the entry lenses with structured light and with illuminating light to illuminate an observed structure with a pattern of the structured light and with the illuminating light;
the light guides being rotatable so that the entry lenses are positioned over the illumination device.

* * * * *